United States Patent [19]

Williams et al.

[11] Patent Number: 5,093,235

[45] Date of Patent: Mar. 3, 1992

[54] IMMUNO-DYE REAGENT AND ASSAY FOR DETECTION OF ENDOTOXIN

[75] Inventors: Taffy J. Williams, Gaithersburg; Che-Hung Lee, Silver Spring, both of Md.; Akindele O. Johnson, Alexandria, Va.

[73] Assignee: The United States of America as represented by the Secretary of the Navy, Washington, D.C.

[21] Appl. No.: 414,224

[22] Filed: Sep. 29, 1989

[51] Int. Cl.$^5$ ............... G01N 33/569; G01N 33/577
[52] U.S. Cl. .................... 435/7.32; 435/38; 435/975; 436/548; 436/808; 436/815
[58] Field of Search ............... 435/4, 7.32, 38, 975; 436/548, 815, 808

[56] References Cited

PUBLICATIONS

"Biological Stains", 7th Ed., H. J. Conn, ed., Williams and Wilkins, Baltimore, (1961), pp. 105–106.
"Staining Procedures", 4th ed, George Clark, ed., Williams and Wilkins, Baltimore, (1981), p. 177.
Johnson et al., "JLN Endotoxin Reagent Assay for Endotoxemia", FASEB Conference, No. 3965, p. A977, Apr. 1988.
Lee et al., "Immunological Approaches in Septic Shock Research", Molecular and Cellular Mechanisms of Septic Shock, pp. 167–173, 1989.
Nachum et al., "Rapid Detection of Gram–Negative Bacterial Meningitis by the Limulus Lysate Test", N. Engl. J. Med., 289:931–934, 1973.
Klein, "Recent Advances in Management of Bacterial Meningitis in Neonates", Infection, 12:S44–S51, 1984.
Kaplan et al., "Rapid Identification of the Invading Microorganism", Pediatric Clinics of North America, 27:783–803, 1980.

Primary Examiner—Esther L. Kepplinger
Assistant Examiner—Susan C. Wolski
Attorney, Agent, or Firm—A. David Spevack; William C. Garvert

[57] ABSTRACT

A novel immuno-dye reagent capable of detecting the presence of endotoxin in samples has been developed. The immuno-dye reagent comprises a solution of new methylene blue and an anti-endotoxin monoclonal antibody specific to a selected endotoxin. The immuno-dye reagent can be used in an assay to detect endotoxin by reacting the immuno-dye reagent with an endotoxin suspect pH adjusted sample, under hydrophobic conditions. The immuno-dye reagent can also be used in any application where binding of endotoxin is crucial, such as purifying endotoxin-contaminated solutions.

4 Claims, No Drawings

IMMUNO-DYE REAGENT AND ASSAY FOR DETECTION OF ENDOTOXIN

BACKGROUND OF THE INVENTION

1. Field of the Invention

This invention relates to a novel immuno-dye reagent and an assay for the detection of endotoxin.

2. Description of the Background Art

Lipopolysaccharide (LPS), an endotoxin, is a major outer membrane component of the cell walls of all Gram-negative bacteria. It is composed of a polysaccharide chain of repeating oligosaccharide units (the O-antigen polysaccharide), a middle core polysaccharide and a lipid-containing moiety (lipid A) by which the LPS macromolecule is anchored in the outer membrane. The O-antigen polysaccharide is composed of repeating oligosaccharide, specific to the species and the strain of the bacteria and the core polysaccharide consists of 11 or less monosaccharide units including three 2-keto-3-deoxyoctonate (KDO). Lipid A usually consists of a phosphorylated glucosamine disaccharide substituted with ester- and amide-linked fatty acids (Brade and Galanos, 1982; Luderitz et al., 1973; Galanos et al., 1985).

The lipid A moiety is embedded in the bacterial membrane while the polysaccharide chain is extruding out of the membrane into hydrophilic surroundings. When LPS is released from bacteria into the aqueous medium, it forms micelles (in the shape of ribbons, disks and lamellae, etc.) and vesicles of bilayer structure with the hydrophobic portion (fatty acid chains) buried and the hydrophilic portion (the phosphate groups, KDO and the polysaccharide chain) exposed to the aqueous medium.

Endotoxins are tenacious contaminants of aqueous and physiological solutions. Endotoxins contaminate medicines and medical devices during preparation processes. They are comparatively heat stable and have a remarkable pyrogenic action (Shenep, J.L. and D.A. Morgan. "Kinetics of Endotoxin Release During Antibiotic Therapy for Experimental Gram-negative Bacterial Sepsis," *J Infect Dis.* 150:380-388, 1984). Bacterial endotoxins have the ability to cause various biological reactions in man and animals such as fever, leukopenia, disseminated intravascular coagulation, endotoxin shock, and death (Luderitz, O., Galanos, C., Lehmann, V., Mayer, H., Rietschel, E.T., and J. Wechersser. "Chemical Structure and Biological Activities of Lipid A's from Various Bacterial Families," *Natur wissenschaften.* 65:578-585,1978).

The death rate from Gram-negative bacteremia and endotoxin remains unacceptably high (30-40%) despite modern advances in antibiotics, pressors and intensive care (Lachman, E., Pitsoe, E., and S.L. Gaffin. "Antilipopolysaccharide Immunotherapy in Management of Septic Shock of Obstetric and Gynecological Origin," *Lancet,* I:981-983, 1984). Lipid A is considered to be the toxic moiety in LPS which participates in the pathogenesis of septic shock exhibiting the pathological effects such as pyrogenicity, activation of coagulation factors, renal failure and hepatocytotoxicity.

The structural diversity of LPS (e.g. the polysaccharide chain) from different origins and its amphipathic property have posed serious difficulties to the prospect of its broad spectrum recognition by immunoglobulins that constitute a critical immunologic defense mechanism among others.

The importance of developing an assay for the detection of endotoxin is illustrated in the case of bacterial meningitis. Despite the availability of potent antibiotics, bacterial meningitis remains an important source of morbidity and mortality (3-30%) in newborns and young children around the world (Marks, M.I. "Bacterial Meningitis in Infants and Children," *Infection,* 12:s52-s55, 1984). It is caused by a variety of Gram-negative and Gram-positive organisms as well as viruses. The principal bacterial etiologic agents are *Haemophilus influenzae. Streptococcus pneumoniae, Staphylococcus aureus. Escherichia coli* and *Neisseria meningitides.* Meningitis presents a medical emergency that requires early medical therapy to prevent death, serious neurologic defects or impaired learning. Speed in establishing the diagnosis and initiating specific therapy is therefore very essential (Klein, J.O. "Recent Advances in Management of Bacterial Meningitis in Neonates," *Infection,* 12:s44-s51, 1984). The recent localized outbreaks of the disease in the U.S. and other regions around the world further suggest the need to improve surveillance (Center for Disease Control. "Summary of Notifiable Diseases, United States, 1987." 1988.).

At present, bacterial meningitis has been detected by countercurrent-immunoelectrophoresis (CIE) of specific polysaccharide antigens in CSF (Kaplan, S.L. and R.D. Feigin. "Rapid Identification of the Invading Microorganism," *Pediatr. Clin. North Am.,* 27:783-803, 1980), Limulus amebocyte lysate assays (Nachum, R., Lipsey, A., and S.E. Siegel. "Rapid Detection of Gram-negative Bacterial Meningitis by the Limulus Lysate Test," *New Engl. J. Med.,* 289:931-934, 1973), standard bacteriological methods, organisms-specific latex agglutination (Severin, W.P.J. "Latex Agglutination in the Diagnosis of Meningicoccal Meningitis," *J. Clin. Pathol.,* 25:1079-1082, 1972) and enzyme-linked immunosorbent assay (ELISA) (Adams, L. B., Henk, M.C., and R.J. Sieberling. "Detection of Vibrio cholerae with Monoclonal Antibodies Specific for Serovar 01 Lipopolysaccharide," *J. Clin. Micro.,* 26:1801-1809, 1988). CIE is capable of detecting some of the infecting organisms, but is limited by the problems of non-specificity, lack of broad specificity and limited sensitivity of polyclonally produced antibodies. Furthermore, it is highly impractical for large numbers of sample or field conditions. Standard bacteriological assay by CSF culture, in contrast, is very reliable but requires prolonged incubation time before results can be available in at least 18 to 24 hours. This is a major disadvantage when prompt detection has been shown to be of great importance to reducing the case fatality rate of meningitis by several investigators (Marks, s52-s55).

The use of the Limulus amoebocyte lysate assay (LAL) for detecting and quantitating endotoxins is well established but, when applied to blood samples, it is restricted because of the presence of various factors in blood that interfere with the LAL endotoxin reaction (Stumacher, R.J., Kovnat, M.J., and W.R. McCabe. "Limitations of the Usefulness of the Limulus Assay for Endotoxin," *N. Engl. J. Med.,* 288:1261-1264, 1973). Also most LAL test methods include periods of one hour or more.

Under many circumstances in both industry and clinical research situations, i.e. pharmaceutical industry, it is highly desirable to be able to identify endotoxin contamination promptly and accurately in non-biological and biological fluids (serum, plasma, cerebrospinal fluid (CSF)). Such a method does not exist at present.

SUMMARY OF THE INVENTION

Accordingly, it is an object of this invention to provide a rapid assay for endotoxin.

It is a further object of this invention to provide an assay for endotoxin that may be carried out in any biological or non-biological solution.

It is a further object of this invention to provide an assay for endotoxin that has a detection limit of less than about 0.1 pg/ml.

It is a further object of this invention to provide a novel immuno-dye reagent.

These and additional objects of the invention are accomplished by mixing an immuno-dye reagent consisting of a dye component and an anti-endotoxin component with a endotoxin-suspect sample under hydrophobic conditions. Once mixed, the sample is checked for a positive reaction indicating the presence of endotoxin or negative reaction.

DETAILED DESCRIPTION OF THE INVENTION

The immuno-dye reagent of the invention comprises two components—new methylene blue, which was found to be an LPS sensitive dye, and anti-endotoxin monoclonal antibodies directed at the highly conserved core oligosaccharide and lipid A regions of the LPS structure. The immuno-dye reagent circumvents the obstacle of antigenic diversity among clinical Gram-negative isolates by providing a uniform reactivity to the broad spectrum of endotoxins in Gram-negative bacteria. Monoclonal antibody is used in the reagent rather than polyclonal in order to overcome the problems encountered by using polyclonals, namely, availability, avidity, and changing characteristics with different bleedings.

The first component of the immuno-dye reagent, new methylene blue, is an aqueous solution of the dye. The concentration is high enough to detect LPS but low enough so that other substances are not detected. Preferably, the dye is in the range of about 0.05% to its saturation concentration. Most preferably, the concentration is about 0.15%. The dye can be in any aqueous LPS-free medium, although LPS-free water is preferred.

The second component of the immuno-dye reagent, anti-endotoxin monoclonal antibody, can be any anti-endotoxin monoclonal antibody that is specific for the suspected endotoxin. Preferably, the anti-endotoxin monoclonal antibody is specifically directed to the core portion of the endotoxin. Most preferably, anti-lipid A monoclonal antibody is used, such as Naval Medical Research Institute strains R14M1 (IgM), R246S1 (IgM), and A78S1 (IgG). Any appropriate LPS-free aqueous medium may be used, but it is preferable to use tissue culture fluid containing a protective substance against microbial growth, such sodium azide at a concentration of about 5 mM.

For the purposes of an assay for endotoxin, the two components of the immuno-dye reagent may be combined prior to the assay or they may be mixed during the assay. It is preferred to mix them during the assay. It is crucial that the two components be free of any pyrogenic materials. One could either remove the pyrogenic materials by an appropriate method such as filtration or centrifugation or one could purchase pyrogen-free components.

The endotoxin-suspect solution to be tested must be at the proper pH since the agglutination of endotoxin is a pH dependent reaction. Preferably, the pH of the endotoxin-suspect solution is adjusted to between about 6.0 to about 8.5, with about 7.4 being most preferred. Often, the sample will not have to be pH adjusted since most closed cavity body fluids have physiological pHs that are within the proper range. However, if the pH needs to be adjusted, pyrogen-free solutions of sodium hydroxide and hydrochloric acid are preferable.

Although any sample size may be used, it is preferable to use a sample size that is practicable and will not waste reagents. Sample size, in the case of biological samples such as CSF, will be dictated by the amount of sample available. Therefore, a sample size of about 20 microliters is most preferred.

The endotoxin assay must be carried out under hydrophobic conditions. Preferably, the assay is carried out on a hydrophobic card, such as a Brewer card. Most preferably, the assay is carried out in an eighteen millimeter circle on the card. As stated earlier, the immuno-dye reagent can be prepared ahead of time and simply mixed with the sample or the two separate components of the immuno-dye reagent can be mixed together with the sample for the assay.

After mixing, the sample is observed for an agglutination reaction. A positive reaction for endotoxin is visible by a slight color change and the presence of a colored precipitate. A negative reaction is visible by a uniformly blue background with no precipitate of any kind. Enough time must be allowed for such a reaction to take place. Preferable, 4 to 10 minutes is sufficient, with about 5 minutes being preferred. A positive (CSF containing about 0.1 ng/ml, for example) and negative (pyrogen free CSF, for example) control must also be run with the assay for comparison.

In addition to the use of the immuno-dye reagent with an assay for endotoxin, the immuno-dye reagent could also be used in any application where binding of the endotoxin is crucial. For example, the immuno-dye reagent could be used in an affinity chromatography system for removing endotoxin from various biological and non-biological solutions.

Having described the invention, the following examples are given to illustrate specific applications of the invention. These specific examples are not intended to limit the scope of the invention described in this application.

EXAMPLE 1

Brewer diagnostic cards, 18 mm circle, were obtained from Hynson, Westcott and Dunning. Standard endotoxin, EC-5, were provided by the U.S. Food and Drug Administration. The dye was obtained from Kodak Chemicals and EM Diagnostics Inc. The chromogenic LAL assay kit was obtained from Whittaker Biochemicals. Pyrogen free water, LPS-free sodium hydroxide and LPS free hydrochloric acid were obtained from Sigma Chemical Company and Travenol Laboratories Inc. Sterile polypropylene plasticwares such as pipet tips, test tubes and eppendorf tubes etc. were used. Siliconized eppendorf tubes were used for preparation of standard LPS dilutions. Sterile 96-well tissue culture plates (polystyrene with lid) were used for the LAL assay.

CLINICAL SPECIMENS

CSF specimens were collected from children during the period between July 1987 and August 1989. Lumbar punctures were performed at Children's Hospital National Medical Center, Washington, D.C. from patients suspected of having meningeal infection. Specimens were stored in sterile, pyrogen-free plastic tubes (Falcon), which were maintained at −70° C. until tested. The present assay and LAL assays were performed independently on coded CSF samples without prior knowledge of the results obtained by the other method.

a. Examination of CSF

Routine processing of CSF specimens included centrifugation, direct Gram-strain of the sediment and culturing by inoculation of the test specimen in appropriate agar or broth medium. The CSF samples were also analyzed for glucose and protein content by standard procedures by the Department of Laboratory Medicine at Children's Hospital National Medical Center, Washington, D.C.

b. Reagents/materials

Anti-lipid A or anti-endotoxin antibodies

Monoclonal antibodies, Naval Medical Research Institute strains R14M1 (IgM), R246S1 (IgM), and A78S1 (IgG) to *Escherichia coli* J5 lipopolysaccharide (LPS) and its lipid A were produced by the method of Kohler and Milstein (Kohler, G. and C. Milstein. "Continuous cultures of fused cells secreting antibody of predefined specificity," Nature, 256:495–497, 1975) and characterized. The specificity and sensitivity of the antibody was established by ELISA, double-immunodiffusion and immunoblotting analysis. Protein concentration was determined by the BCA Protein assay and Bradford microassay procedure (Bradford, M.M. "A rapid and sensitive method for the quantitation of microgram quantities of protein utilizing the principle of protein-dye binding," Ann. Biochem., 72:248–254, 1976) with mouse myeloma protein as reference standard.

Assay reagent

The assay reagent consisted of two components. The first component was 0.15% new methylene blue in LPS-free water. The second component was the anti-lipid A or anti-endotoxin monoclonal antibodies (see above) in tissue culture fluid containing 5 mM sodium azide. Prior to use, the dye and antibody solutions were separately centrifuged at 20,000×g for 20 minutes at 4° C. in pyrogen-free centrifuge tubes. Supernatant solutions of dye and antibody were stored at room temperature and 4° C. respectively.

Standard endotoxin solutions

Clinically defined, bacteriologically sterile and endotoxin-free CSF specimens were combined and used for preparation of various concentrations of the United States standard endotoxin, EC-5 (0 to 500 ug/ml). Each concentration was assayed by the procedure below in order to evaluate the sensitivity of the assay.

c. Assay procedure

Agglutination testing was performed by mixing 20 ul CSF test sample with 10 ul dye solution and 20 ul antibody solution, both of which had been experimentally defined as optional reactivity concentrations for rapid agglutination of endotoxins in CSF, on a hydrophobic Brewer diagnostic card (18 mm circle), followed by rotation on clinical rotator at 130±2 RPM (Fisher Scientific Co.) or by hand. A positive reaction was visualized after 5 min by a slight color change and the presence of colored precipitate. Negative reactions showed uniformly blue background with no precipitates of any kind. With each group of test samples assayed, a positive (CSF containing 0.1 ng/ml endotoxin) and a negative control (pyrogen free CSF) were run concurrently. A negative test was further confirmed by addition of endotoxin to the test-sample and retesting to get a positive test. Unpredictable presence of any possible inhibitory substances in the test sample was similarly ruled out.

Since the agglutination of endotoxin is a pH dependent reaction, with optimum pH of 6.0 to 8.5, use of solutions buffered to this range were found to increase the sensitivity of the assay against standard endotoxin solutions. Furthermore, the salt concentration in test samples should be within physiological conditions while temperatures of 20° C. to 25° C. were found to be adequate. Salt concentrations of 0.2 M or above were inhibitory to the JLN assay.

Obviously, many modifications and variations of the present invention are possible in light of the above teachings. It is therefore to be understood that within the scope of the appended claims, the invention may be practiced otherwise than as specifically described.

What we claim is:

1. An immuno-dye reagent for detecting endotoxin comprising a solution of between 0.05% and the saturation concentration of new methylene blue and a solution of an anti-endotoxin monoclonal antibody specific to the highly conserved core oligosaccharide or the Lipid A regions of said endotoxin.

2. An immuno-dye reagent as described in claim 1 wherein the concentration of new methylene blue is about 0.15%.

3. An immuno-dye reagent as described in claim 1 wherein the anti-endotoxin monoclonal antibody is one that is specifically directed to the Lipid A region of the suspected endotoxin.

4. An immuno-dye reagent as described in claim 2 wherein the anti-endotoxin monoclonal antibody is one that is specifically directed to the Lipid A region of the suspected endotoxin.

* * * * *